US012799510B2

(12) United States Patent
Shin et al.

(10) Patent No.: US 12,799,510 B2
(45) Date of Patent: Nov. 17, 2026

(54) ZINC-BINDING DEHYDROGENASE VARIANT AND METHOD FOR PRODUCING L-AROMATIC AMINO ACID USING SAME

(71) Applicant: DAESANG CORPORATION, Seoul (KR)

(72) Inventors: Won Joo Shin, Gyeonggi-do (KR); Jae Eun Park, Incheon (KR); Yong Soo Kim, Gyeonggi-do (KR); Young Il Jo, Seoul (KR)

(73) Assignee: DAESANG CORPORATION, Seoul (KR)

( * ) Notice: Subject to any disclaimer, the term of this patent is extended or adjusted under 35 U.S.C. 154(b) by 111 days.

(21) Appl. No.: 18/838,704

(22) PCT Filed: Jul. 11, 2022

(86) PCT No.: PCT/KR2022/010045
§ 371 (c)(1),
(2) Date: Sep. 16, 2024

(87) PCT Pub. No.: WO2023/158030
PCT Pub. Date: Aug. 24, 2023

(65) Prior Publication Data

US 2026/0176662 A1 Jun. 25, 2026

(30) Foreign Application Priority Data

Feb. 16, 2022 (KR) ........................ 10-2022-0020010

(51) Int. Cl.
*C12P 13/22* (2006.01)
*C12N 9/04* (2006.01)
*C12N 15/70* (2006.01)

(52) U.S. Cl.
CPC .......... *C12P 13/222* (2013.01); *C12N 9/0006* (2013.01); *C12N 15/70* (2013.01); *C12P 13/227* (2013.01); *C12N 2800/101* (2013.01)

(58) Field of Classification Search
CPC ....... C12P 13/222; C12P 13/227; C12P 13/04; C12P 13/22; C12N 9/0006; C12N 15/70; C12N 2800/101; C12N 15/52; C12N 9/0004; C12R 2001/19
See application file for complete search history.

(56) References Cited

FOREIGN PATENT DOCUMENTS

| | | |
|---|---|---|
| KR | 10-2006-0127990 | 12/2006 |
| KR | 10-1830002 | 2/2018 |
| KR | 10-1947959 | 2/2019 |

OTHER PUBLICATIONS

International Search Report issued Nov. 11, 2022 in International (PCT) Application No. PCT/KR2022/010045.
Gu, Pengfei et al., "The improved L-tryptophan production in recombinant *Escherichia coli* by expressing the polyhydroxybutyrate synthesis pathway", Appl Microbiol Biotechnol, 2013, vol. 97, pp. 4121-4127.
Li, Jianghui et al., "Zinc Toxicity and Iron-Sulfur Cluster Biogenesis in *Escherichia coli*", Applied and Environmental Microbiology, May 2019, vol. 85, Issue 9, pp. 1-13.
Accession No. WP_000853247.1, zinc-binding dehydrogenase [Enterobacteriaceae], NCBI GenBank, Dec. 16, 2020.

*Primary Examiner* — Ganapathirama Raghu
(74) *Attorney, Agent, or Firm* — Wenderoth, Lind & Ponack, L.L.P.

(57) ABSTRACT

The present invention relates to a novel zinc-binding dehydrogenase variant and a method of producing an L-aromatic amino acid using the same. The zinc-binding dehydrogenase variant is obtained by substituting one or more amino acids in the amino acid sequence constituting zinc-binding dehydrogenase to change the enzymatic activity of the zinc-binding dehydrogenase, and a recombinant microorganism comprising the variant is capable of efficiently producing an L-aromatic amino acid.

7 Claims, 2 Drawing Sheets

Specification includes a Sequence Listing.

ZINC-BINDING DEHYDROGENASE VARIANT AND METHOD FOR PRODUCING L-AROMATIC AMINO ACID USING SAME

SEQUENCE LISTING

A sequence listing in electronic (XML file) format is filed with this application and incorporated herein by reference. The name of the XML file is "Sequence_listing-1211A.xml"; the file was created on Aug. 15, 2024; the size of the file is 38,285 bytes.

TECHNICAL FIELD

The present invention relates to a novel zinc-binding dehydrogenase variant and a method of producing an L-aromatic amino acid using the same.

BACKGROUND ART

Amino acids are classified into hydrophobic, hydrophilic, basic, and acidic amino acids, depending on the nature of their side chains, and among them, amino acids having a benzene ring are called aromatic amino acids.

Aromatic amino acids include phenylalanine, tyrosine, and tryptophan. Phenylalanine and tryptophan are essential amino acids that are not synthesized in vivo and correspond to high value-added industries that form a global market worth $300 billion annually.

For the production of aromatic amino acids, either naturally occurring wild-type strains or mutant strains modified to have an increased ability to produce amino acids may be used. In recent years, in order to improve the efficiency of production of aromatic amino acids, there has been development of a variety of recombinant strains or mutant strains having excellent L-aromatic amino acid productivity by applying genetic recombination technology to microorganisms such as *Escherichia coli* and *Corynebacterium*, which are widely used in the production of useful substances such as L-amino acids, and methods of producing L-aromatic amino acids using the same. In particular, there have been attempts to increase the production of L-aromatic amino acids by targeting genes such as enzymes, transcription factors and transport proteins, which are involved in the biosynthetic pathways of L-aromatic amino acids, or by inducing mutations in promoters that regulate the expression of these genes. However, there are dozens of types of proteins such as enzymes, transcription factors and transport proteins, which are involved directly or indirectly in the production of L-aromatic amino acids, and thus much research is still needed on the increase in L-aromatic amino acid productivity by changes in the activity of these proteins.

PRIOR ART DOCUMENTS

Patent Documents

Korean Patent No. 10-1830002

DISCLOSURE

Technical Problem

An object of the present invention is to provide a novel zinc-binding dehydrogenase variant.

Another object of the present invention is to provide a polynucleotide encoding the variant.

Still another object of the present invention is to provide a transformant comprising the variant or the polynucleotide.

Yet another object of the present invention is to provide a method of producing an L-aromatic amino acid using the transformant.

Technical Solution

One aspect of the present invention provides a zinc-binding dehydrogenase variant consisting of the amino acid sequence of SEQ ID NO: 1 in which glycine at position 102 in the amino acid sequence of SEQ ID NO: 3 is substituted with arginine.

The "zinc-binding dehydrogenase" as used in the present invention is a type of zinc-binding oxidoreductase that exhibits redox activity in the presence of NAD or NADP. The zinc-binding dehydrogenase may be a gene encoding zinc binding dehydrogenase or a sequence having substantial identity thereto. As used herein, "substantial identity" means that, when each gene sequence, i.e., a base sequence or nucleotide sequence, and any other nucleotide sequence are aligned to correspond to each other as much as possible and analyzed, the other nucleotide sequence has a sequence homology of at least 70%, at least 80%, at least 90%, or at least 98% with each nucleotide sequence.

The zinc-binding dehydrogenase in the present invention is encoded by the yggP gene and comprises the amino acid sequence of SEQ ID NO: 3.

According to one embodiment of the present invention, the amino acid sequence of SEQ ID NO: 3 may be derived from wild-type *E. coli*.

As used in the present invention, the term "variant" refers to a polypeptide which is obtained by conservative substitution and/or modification of one or more amino acids at the N-terminus, C-terminus of and/or within the amino acid sequence of a specific protein and has an amino acid sequence different from that of the protein, but retains functions or properties of the protein. As used herein, the term "conservative substitution" means replacing one amino acid with another amino acid having similar structural and/or chemical properties. The conservative substitution may have little or no impact on the activity of the protein or polypeptide. In addition, some variants include those in which one or more portions, such as an N-terminal leader sequence or transmembrane domain, have been removed, or those in which a portion has been removed from the N- and/or C-terminus of a mature protein. The ability of the variant may be increased, unchanged, or reduced compared to that of the polypeptide before modification. In the present invention, the term "variant" may be used interchangeably with terms such as variant type, modification, variant polypeptide, mutated protein, mutation, and the like.

The variant in the present invention may be a zinc-binding dehydrogenase variant consisting of the amino acid sequence of SEQ ID NO: 1 in which the amino acid glycine at position 102 in the amino acid sequence of SEQ ID NO: 3 is substituted with arginine.

Another aspect of the present invention provides a polynucleotide encoding the zinc-binding dehydrogenase variant.

As used in the present invention, the term "polynucleotide" refers to a DNA or RNA strand having a certain length or more, which is a long-chain polymer of nucleotides formed by linking nucleotide monomers via covalent bonds. More specifically, the term "polynucleotide" refers to a polynucleotide fragment encoding the variant.

The polynucleotide may comprise a nucleotide sequence encoding the amino acid sequence of SEQ ID NO: 1.

According to one embodiment of the present invention, the polynucleotide may comprise the nucleotide sequence represented by SEQ ID NO: 2.

Still another aspect of the present invention provides a vector comprising a polynucleotide encoding the zinc-binding dehydrogenase variant.

Yet another aspect of the present invention provides a transformant comprising the zinc-binding dehydrogenase variant or the polynucleotide.

As used in the present invention, the term "vector" refers to any type of nucleic acid sequence transfer structure that is used as a means for transferring and expressing a gene of interest in a host cell. Unless otherwise specified, the term "vector" may mean one allowing the nucleic acid sequence contained therein to be expressed after insertion into the host cell genome and/or one allowing the nucleic acid sequence to be expressed independently. This vector comprises essential regulatory elements operably linked so that an inserted gene can be expressed. As used herein, the term "operably linked" means that a gene of interest and sequences for regulating expression of the gene are functionally linked together in a manner enabling gene expression, and the term "regulatory elements" include a promoter for initiating transcription, any operator sequence for regulating transcription, a sequence encoding suitable mRNA ribosome-binding sites, and a sequence for regulating termination of transcription and translation.

The vector that is used in the present invention is not particularly limited as long as it may replicate in a host cell, and any vector known in the art may be used. Examples of the vector include a natural or recombinant plasmid, cosmid, virus and bacteriophage. Examples of a phage vector or cosmid vector include, but are not limited to, pWE15, M13, λMBL3, λMBL4, λIXII, λASHII, λAPII, λt10, λt11, Charon4A, and Charon21A, and examples of a plasmid vector include, but are not limited to, pBR series, pUC series, pBluescriptII series, pGEM series, pTZ series, pCL series, and pET series.

The vector may typically be constructed as a vector for cloning or as a vector for expression. The vector for expression may be a conventional vector that is used in the art to express a foreign gene or protein in a plant, animal, or microorganism, and may be constructed through various methods known in the art.

The recombinant vector may be constructed to use a prokaryotic or eukaryotic cell as a host. For example, when the vector used is an expression vector and uses a prokaryotic cell as a host, the vector generally comprises a strong promoter capable of promoting transcription (e.g., pLλ promoter, CMV promoter, trp promoter, lac promoter, tac promoter, T7 promoter, etc.), a ribosome binding site for initiation of translation, and a transcription/translation termination sequence. When a eukaryotic cell is used as a host, the vector comprises a replication origin operating in the eukaryotic cell, such as an f1 replication origin, an SV40 replication origin, a pMB1 replication origin, an adeno replication origin, an AAV replication origin, or a BBV replication origin, without being limited thereto. In addition, the recombinant vector may comprise a promoter derived from the genome of a mammalian cell (e.g., metallothionein promoter) or a promoter derived from a mammalian virus (e.g., adenovirus late promoter, vaccinia virus 7.5K promoter, SV40 promoter, cytomegalovirus promoter, HSV-tk promoter, etc.), and generally has a polyadenylation sequence as a transcription termination sequence.

The recombinant vector may comprise a selection marker. The selection marker serves to select a transformant (host cell) transformed with the vector, and since only cells expressing the selection marker can survive in the medium treated with the selection marker, it is possible to select transformed cells. Representative examples of the selection marker include, but are not limited to, kanamycin, streptomycin, and chloramphenicol.

The transformant may be produced by inserting the recombinant vector into a host cell, and the transformant may be obtained by introducing the recombinant vector into an appropriate host cell. The host cell is a cell capable of stably and continuously cloning or expressing the expression vector, and any host cell known in the art may be used.

When the vector is transformed into prokaryotic cells to generate recombinant microorganisms, examples of host cells that may be used include, but are not limited to, *E. coli* sp. strains such as *E. coli* JM109, *E. coli* BL21, *E. coli* RR1, *E. coli* LE392, *E. coli* B, *E. coli* X 1776, *E. coli* W3110, and *E. coli* XL1-Blue, *Bacillus* sp. strains such as *Bacillus subtilis*, and *Bacillus thuringiensis*, and various Enterobacteriaceae strains such as *Salmonella typhimurium, Serratia marcescens*, and *Pseudomonas* species.

When the vector is transformed into eukaryotic cells to generate recombinant microorganisms, examples of host cells that may be used include, but are not limited to, yeast (e.g., *Saccharomyces cerevisiae*), insect cells, plant cells and animal cells, such as Sp2/0, CHO K1, CHO DG44, PER. C6, W138, BHK, COS7, 293, HepG2, Huh7, 3T3, RIN, and MDCK cell lines.

As used in the present invention, the term "transformation" refers to a phenomenon in which external DNA is introduced into a host cell, thereby artificially causing genetic changes, and the term "transformant" refers to a host cell into which external DNA has been introduced and in which the expression of the gene of interest is stably maintained.

The transformation may be performed using a suitable vector introduction technique selected depending on the host cell, so that the gene of interest or a recombinant vector comprising the same may be expressed in the host cell. For example, introduction of the vector may be performed by electroporation, heat-shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or any combination thereof, without being limited thereto. As long as the transformed gene may be expressed in the host cell, it may be integrated into and placed in the chromosome of the host cell, or it may exist extrachromosomally, without being limited thereto.

The transformant may include a cell transfected, transformed, or infected with the recombinant vector of the present disclosure in vivo or in vitro, and may be used in the same sense as a recombinant host cell, a recombinant cell, or a recombinant microorganism.

According to one embodiment of the present invention, the transformant may be an *Escherichia* sp. strain.

Examples of the *Escherichia* sp. strain include, but are not limited to, *Escherichia coli, Escherichia albertii, Escherichia blattae, Escherichia fergusonii, Escherichia hermannii, Escherichia vulneris*, and the like.

The transformant in the present invention may be a strain either comprising the above-described zinc-binding dehydrogenase variant or a polynucleotide encoding the same or comprising the vector comprising the same, a strain expressing the zinc-binding dehydrogenase variant or the polynucleotide, or a strain having activity for the zinc-binding dehydrogenase variant, without being limited thereto.

According to one embodiment of the present invention, the transformant may have the ability to produce an L-aromatic amino acid.

The transformant may naturally have the ability to produce an L-aromatic amino acid or may be one artificially endowed with the ability to produce an L-aromatic amino acid.

According to one embodiment of the present invention, the transformant may have an increased ability to produce an L-aromatic amino acid, due to a change in the activity of zinc-binding dehydrogenase.

As used in the present invention, the term "increased ability to produce" means that L-aromatic amino acid productivity has increased compared to that of the parent strain. As used herein, the term "parent strain" refers to a wild-type strain or mutant strain to be mutated, and includes a strain that is to be mutated directly or to be transformed with a recombinant vector or the like. In the present invention, the parent strain may be a wild-type *Escherichia* sp. strain or an *Escherichia* sp. strain mutated from the wild-type strain.

The transformant according to the present invention exhibits an increased ability to produce an L-aromatic amino acid compared to the parent strain, due to a change in the activity of zinc-binding dehydrogenase by introduction of the zinc-binding dehydrogenase variant thereinto. In particular, the amount of L-aromatic amino acid produced by the transformant may be at least 5%, specifically 5 to 60% (preferably 10 to 50%) higher than that produced by the parent strain, and the transformant is capable of producing 4 to 20 g of an L-aromatic amino acid per liter of a culture of the strain.

Still yet another aspect of the present invention provides a method for producing an L-aromatic amino acid, comprising steps of: culturing the transformant in a medium; and recovering an L-aromatic amino acid from the transformant or the medium in which the transformants has been cultured.

The culturing may be performed using a suitable medium and culture conditions known in the art, and any person skilled in the art may easily adjust and use the medium and the culture conditions. Specifically, the medium may be a liquid medium, without being limited thereto. Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For the culture medium for the *Escherichia* sp. strain, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, without being limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20 °C to 45 °C, for example, 25 °C to 40 °C. The culturing may be continued until a desired amount of a useful substance is produced. For example, the culturing time may be 10 hours to 160 hours.

According to one embodiment of the present invention, in the step of recovering an L-aromatic amino acid from the cultured transformant or the medium in which the transformant has been cultured, the produced L-aromatic amino acid may be collected or recovered from the medium using a suitable method known in the art depending on the culture method. Examples of a method that may be used to recover the produced L-aromatic amino acid include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present invention, the step of recovering an L-aromatic amino acid may be performed by centrifuging the culture medium at a low speed to remove biomass and separating the obtained supernatant through ion-exchange chromatography.

According to one embodiment of the present invention, the step of recovering an L-aromatic amino acid may include a process of purifying the L-aromatic amino acid.

According to one embodiment of the present invention, the L-aromatic amino acid may be at least one selected from the group consisting of L-tryptophan, L-phenylalanine, and L-tyrosine.

Advantageous Effects

The zinc-binding dehydrogenase variant according to the present invention is obtained by substituting one or more amino acids in the amino acid sequence constituting zinc-binding dehydrogenase to change the enzymatic activity of the zinc-binding dehydrogenase, and a recombinant microorganism comprising the zinc-binding dehydrogenase variant is capable of efficiently producing an L-aromatic amino acid.

MODE FOR INVENTION

Figure 1:
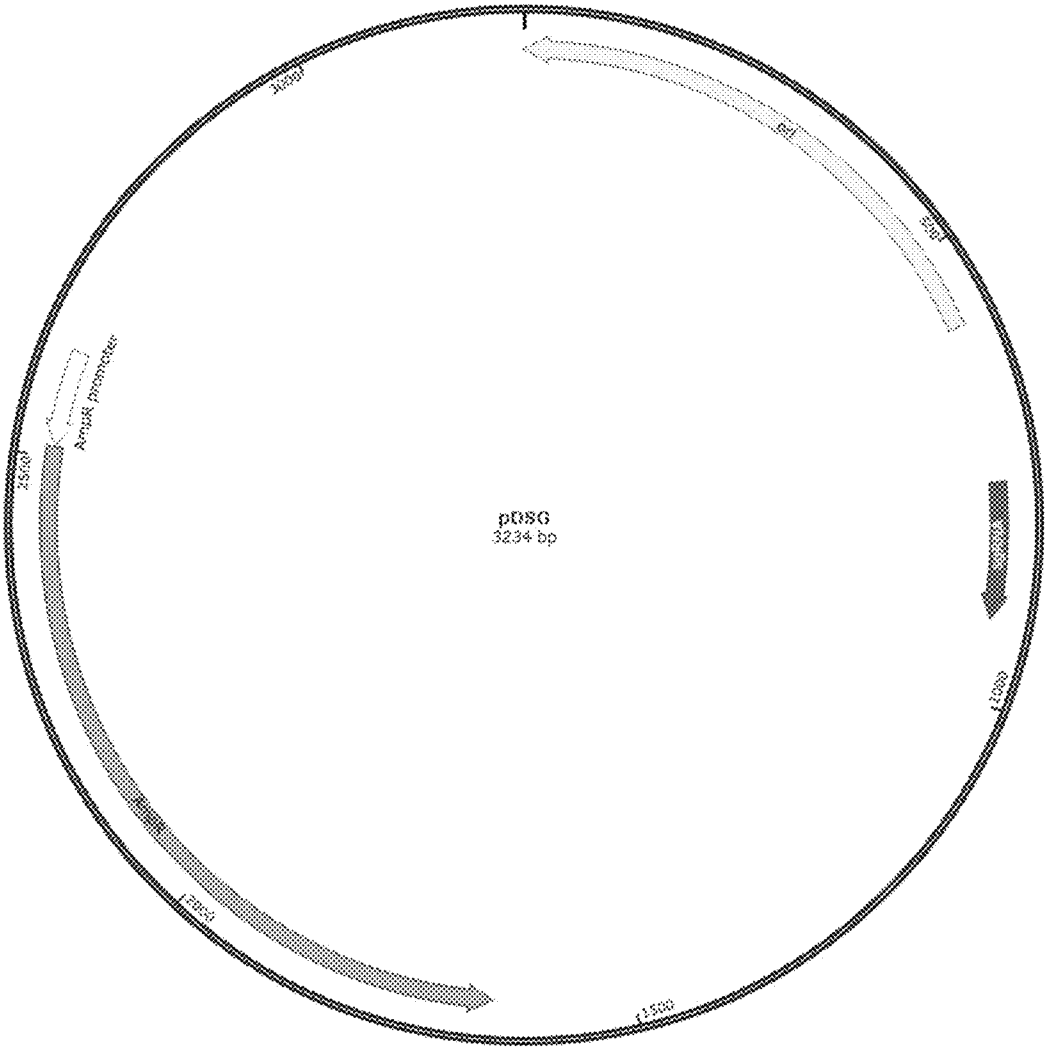
FIG. 1 shows the structure of plasmid pDSG according to one embodiment of the present invention.
Figure 2:
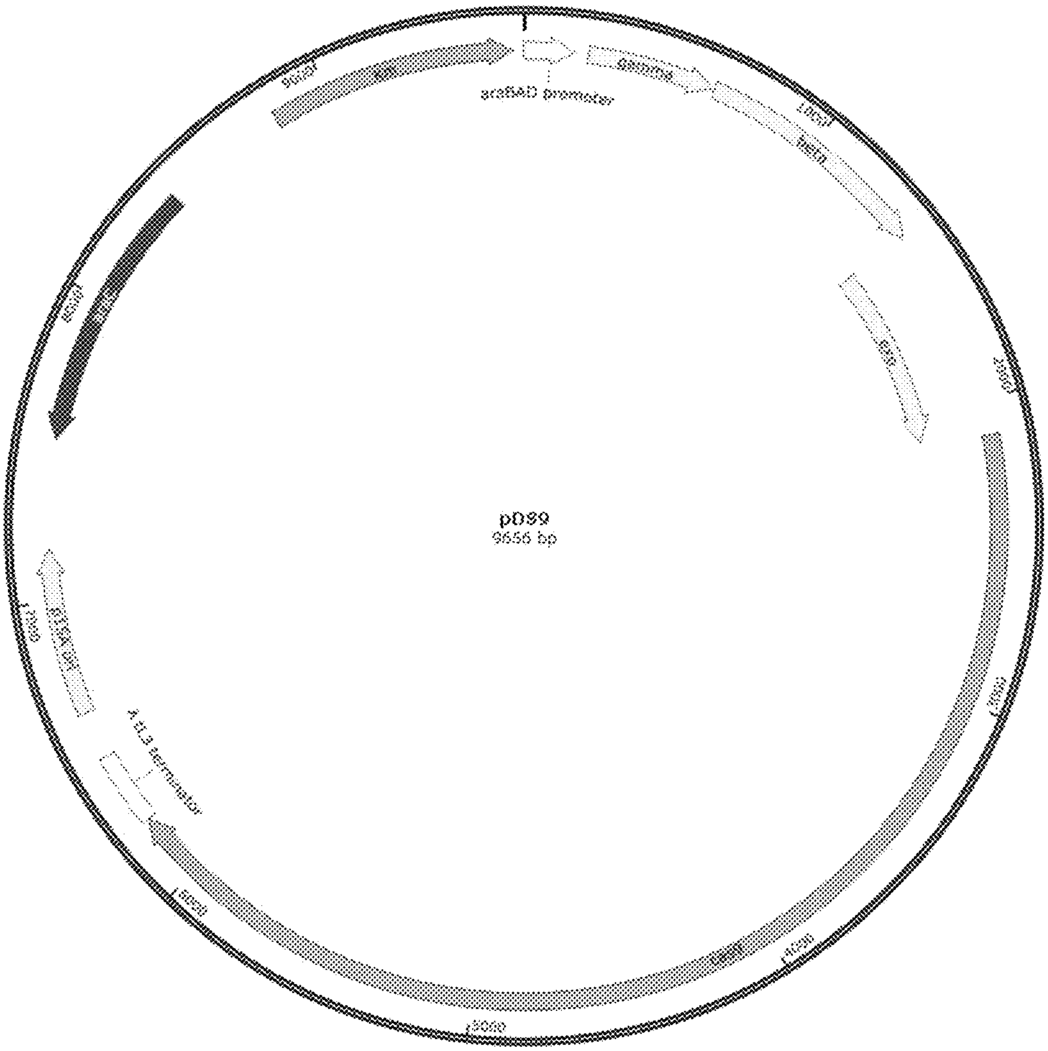
FIG. 2 shows the structure of plasmid pDS9 according to one embodiment of the present invention.

Hereinafter, the present invention will be described in more detail. However, this description is merely presented by way of example to facilitate the understanding of the present invention, and the scope of the present invention is not limited by this exemplary description.

Example 1. Construction of Strains Expressing Zinc-Binding Dehydrogenase Variant In order to evaluate the effect of a variant resulting from substitution of arginine for glycine at position 102 of the amino acid sequence of zinc-binding dehydrogenase (SEQ ID NO: 3) on the production of L-aromatic amino acids, a vector expressing the zinc-binding dehydrogenase variant and strains into which the vector has been introduced were constructed. For insertion of the gene encoding the zinc-binding dehydrogenase variant into the strains, plasmids pDSG and pDS9 were used, and the strains were constructed as follows.

Here, the plasmid pDSG has an origin of replication that works only in *Escherichia coli*, contains an ampicillin resistance gene, and has a mechanism for expressing guide RNA (gRNA). The plasmid pDS9 has an origin of replication that works only in *Escherichia coli*, contains a kanamycin resistance gene and λ red genes (exo, bet and gam), and has a mechanism for expressing CAS9 derived from *Streptococcus pyogenes*.

1-1. Construction of Vector pDSG-yggP (Gly102Arg) for Transformation

Using *Escherichia coli* MG1655 (KCTC14419BP) gDNA as a template, a fragment upstream of the amino acid mutation at position 102 of the *E. coli* yggP gene encoding zinc-binding dehydrogenase was obtained by PCR using a primer pair of primer 7 and primer 9 and a primer pair of primer 8 and primer 10, and a fragment downstream of the amino acid mutation at position 102 of the *E. coli* yggP gene was obtained by PCR using a primer pair of primer 11 and primer 13 and a primer pair of primer 12 and primer 14. At this time, each of the upstream and downstream fragments contained a sequence that modifies glycine (Gly) at amino acid residue position 102 of the yggP gene into arginine (Arg). In the PCR, Takara PrimeSTAR Max DNA polymerase was used as polymerase, and PCR amplification was performed for 30 cycles under the following conditions: denaturation at 95 °C for 10 sec, annealing at 57 °C for 15 sec, and polymerization at 72 °C for 10 sec.

Using the plasmid pDSG as a template, four pDSG gene fragments were obtained by PCR using a primer pair of primer 3 and primer 5, a primer pair of primer 4 and primer 6, a primer pair of primer 15 and primer 1, and a primer pair of primer 16 and primer 2, respectively. At this time, each of the gene fragments contained a gRNA sequence targeting Gly at position 102 of the yggP gene. The gRNA was selected as a 20 mer upstream of NGG of the sequence to be mutated. In the PCR, Takara PrimeSTAR 1 Max DNA polymerase was used as polymerase, and PCR amplification was performed for 30 cycles under the following conditions: denaturation at 95 °C for 10 sec, annealing at 57 °C for 15 sec, and polymerization at 72 °C for 15 sec.

The obtained fragments upstream and downstream of the amino acid at position 102 of the yggP gene, and the obtained four pDSG gene fragments were cloned using a self-assembly cloning method (BioTechniques 51:55-56 (July 2011)), thereby obtaining a recombinant plasmid which was named pDSG-yggP (Gly102Arg).

1-2. Construction of L-Tryptophan- or L-Phenylalanine-Producing Strain into which Zinc-Binding Dehydrogenase Variant yggP (Gly102Arg) has been Introduced To construct an L-tryptophan-producing strain and an L-phenylalanine-producing strain, *Escherichia coli* KFCC11660P and KCCM10016 were used as parent strains.

The KFCC11660P strain or the KCCM10016 strain was primarily transformed with the plasmid pDS9 and cultured in LB-Km (containing 25 g/L of LB liquid medium and 50 mg/L of kanamycin) solid medium, and then kanamycin-resistant colonies were selected. The selected colonies were secondarily transformed with the pDSG-yggP (Gly102Arg) plasmid and cultured in LB-Amp & Km (containing 25 g/L of LB liquid medium, 100 mg/L of ampicillin and 50 mg/L of kanamycin) solid medium, and then ampicillin- and kanamycin-resistant colonies were selected. Next, a gene fragment was obtained by PCR using a primer pair of primer 17 and primer 18. Here, Takara PrimeSTAR Max DNA polymerase was used as polymerase, and PCR amplification was performed for 30 cycles under the following conditions: denaturation at 95 °C for 10 sec, annealing at 57 °C for 10 sec, and polymerization at 72 °C for 15 sec. The sequence of the gene fragment obtained using the primer pair of primer 17 and primer 18 was analyzed by Macrogen.

The selected secondary transformants were passaged 7 times in LB liquid medium, and colonies were selected on LB solid medium. Each colony was selectively cultured on each of LB, LB-Amp and LB-Km solid media. Colonies that did not grow on the LB-Amp and LB-Km solid media while growing on the LB solid medium were selected. The strains constructed in this way were named KFCC11660P_yggP (Gly102Arg) and KCCM10016_yggP (Gly102Arg), respectively.

The primer sequences used in Example 1 are shown in Table 1 below.

TABLE 1

| Primer name | SEQ ID NO. | Primer sequence (5'→3') |
|---|---|---|
| Primer 1 | 5 | CAATTTTATTATAGTAATTGACTATTATAC |
| Primer 2 | 6 | GCTTGGTAACCAATTTTATTATAGTAATTG ACTATTATAC |
| Primer 3 | 7 | GTTACCAAGCGGATATTCAGGTTTTAGAGC TAGAAATAGC |
| Primer 4 | 8 | GGATATTCAGGTTTTAGAGCTAGAAATAGC |
| Primer 5 | 9 | GAGCCTGTCGGCCTACCTGCT |
| Primer 6 | 10 | CGGCCGGCATGAGCCTGTCG |
| Primer 7 | 11 | ATGCCGGCCGGCTGCTATTTATGGCAAGCG |
| Primer 8 | 12 | GCTGCTATTTATGGCAAGCG |

TABLE 1-continued

| Primer name | SEQ ID NO. | Primer sequence (5'→3') |
|---|---|---|
| Primer 9 | 13 | CCCATCGCCGGTTGCAATAC |
| Primer 10 | 14 | GCTTGGTAACCCCATCGCCG |
| Primer 11 | 15 | GTTACCAAGCAGATATTCAGCGGGCTACAG |
| Primer 12 | 16 | AGATATTCAGCGGGCTACAG |
| Primer 13 | 17 | TGCTCATAAACATATTGCGT |
| Primer 14 | 18 | GCCCATGCGATGCTCATAAA |
| Primer 15 | 19 | TCGCATGGGCGAGCTCCTGAAAATCTCGAT AAC |
| Primer 16 | 20 | GAGCTCCTGAAAATCTCGATAAC |
| Primer 17 | 21 | ACGTGTGACGGATAAACCAC |
| Primer 18 | 22 | TTCACATACACCAGCTCAAT |

Experimental Example 1. Evaluation of L-Aromatic Amino Acid Productivity of Mutant Strain into Which Zinc-Binding Dehydrogenase Variant has been Introduced The L-tryptophan or L-phenylalanine productivities of the parent strains (KFCC11660P and KCCM10016) and the mutant strains (KFCC11660P_yggP (Gly102Arg) and KCCM10016_yggP (Gly102Arg)) into which the zinc-binding dehydrogenase variant has been introduced were compared.

1 vol % of each strain (parent strain or mutant strain) was inoculated into a 100-mL flask containing 10 mL of a medium for tryptophan production or a medium for phenylalanine production (the composition of each medium is shown in Table 2 below) and was cultured with shaking at 37 °C and 200 rpm for 72 hours. After completion of the culturing, the concentration of L-tryptophan or L-phenylalanine in the medium was measured using HPLC (Agilent), and the results are shown in Tables 3 and 4 below, respectively.

TABLE 2

| Medium for tryptophan production | | Medium for phenylalanine production | |
|---|---|---|---|
| Component | Content | Component | Content |
| Glucose | 80.0 g/L | Glucose | 80.0 g/L |
| $(NH_4)_2SO_4$ | 20.0 g/L | $(NH_4)_2SO_4$ | 20.0 g/L |
| $K_2HPO_4$ | 0.8 g/L | $K_2HPO_4$ | 1.0 g/L |
| $K_2SO_4$ | 0.4 g/L | $KH_2PO_4$ | 1.0 g/L |
| $MgCl_2$ | 0.8 g/L | $K_2SO_4$ | 0.4 g/L |
| Fumaric acid | 1.0 g/L | $MgCl_2$ | 1.0 g/L |

TABLE 2-continued

| Medium for tryptophan production | | Medium for phenylalanine production | |
|---|---|---|---|
| Component | Content | Component | Content |
| Yeast extract | 1.0 g/L | Fumaric acid | 0.5 g/L |
| $(NH_4)_6Mo_7O_{24}$ | 0.12 ppm | Yeast extract | 1.0 g/L |
| $H_3BO_3$ | 0.01 ppm | Glutamic acid | 0.5 g/L |
| $CuSO_4$ | 0.01 ppm | $CaCl_2$ | 5.00 ppm |
| $MnCl_2$ | 2.00 ppm | $MnCl_2$ | 2.00 ppm |
| $ZnSO_4$ | 0.01 ppm | $ZnSO_4$ | 1.00 ppm |
| $CoCl_2$ | 0.10 ppm | $CoCl_2$ | 0.10 ppm |
| $FeCl_2$ | 10.00 ppm | $FeCl_2$ | 10.00 ppm |
| Thiamine_HCl | 20.00 ppm | Thiamine_HCl | 20.00 ppm |
| L-Tyrosine | 200.00 ppm | L-Tyrosine | 200.00 ppm |
| L-phenylalanine | 300.00 ppm | $CaCO_3$ | 3% |
| $CaCO_3$ | 3% | — | — |
| pH 7.0 with NaOH (33%) | | pH 7.0 with NaOH (33%) | |

TABLE 3

| Strain | L-tryptophan concentration (g/L) | L-tryptophan concentration increase rate (%) |
|---|---|---|
| KFCC11660P | 4.10 | — |
| KFCC11660P_yggP (Gly102Arg) | 4.87 | 18.7 |

TABLE 4

| Strain | L-phenylalanine concentration (g/L) | L-phenylalanine concentration increase rate (%) |
|---|---|---|
| KCCM10016 | 3.42 | — |
| KCCM10016_yggP (Gly102Arg) | 4.21 | 23.1 |

As shown in Tables 3 and 4 above, it was confirmed that the mutant strains KFCC11660P_yggP (Gly102Arg) and KCCM10016_yggP (Gly102Arg) into which the zinc-binding dehydrogenase variant has been introduced showed increases in L-tryptophan production and L-phenylalanine production of about 19% and 23%, respectively, compared to the parent strains KFCC11660P and KCCM10016.

So far, the present invention has been described with reference to the embodiments. Those skilled in the art will appreciate that the present invention can be implemented in modified forms without departing from the essential features of the present invention. Therefore, the disclosed embodiments should be considered in descriptive sense only and not for purposes of limitation. Therefore, the scope of the present invention is defined not by the detailed description of the present invention but by the appended claims, and all differences within a range equivalent to the scope of the appended claims should be construed as being included in the present invention.

The invention claimed is:

1. A zinc-binding dehydrogenase variant consisting of the amino acid sequence of SEQ ID NO: 1 in which glycine at position 102 in the amino acid sequence of SEQ ID NO: 3 is substituted with arginine.

2. A isolated polynucleotide encoding the variant of claim 1.

3. A transformant comprising the variant of claim 1 or a polynucleotide encoding said variant.

4. The transformant of claim 3, which is an *Escherichia* sp. strain.

5. The transformant of claim 3, which has ability to produce an L-aromatic amino acid.

6. A method for producing an L-aromatic amino acid, comprising steps of:

culturing the transformant of claim 3 in a medium; and recovering an L-aromatic amino acid from the transformant or the medium in which the transformant has been cultured.

7. The method of claim 6, wherein the L-aromatic amino acid is at least one selected from the group consisting of L-tryptophan, L-phenylalanine, and L-tyrosine.

* * * * *

SEQUENCE LISTING

```
Sequence total quantity: 24
SEQ ID NO: 1            moltype = AA  length = 425
FEATURE                 Location/Qualifiers
source                  1..425
                        mol_type = protein
                        organism = synthetic construct
SEQUENCE: 1
```

-continued

```
MKTKVAAIYG KRDVRLRVFE LPEITDNELL VSVISDSVCL STWKAALLGS EHKRVPDDLE  60
NHPVITGHEC AGVIVEVGKN LTGKYKKGQR FVLQPAMGLP SRYSAGYSYE YFGGNATYMI  120
IPEIAINLGC VLPYHGSYFA AASLAEPMCC IIGAYHANYH TTQYVYEHRM GVKPGGNIAL  180
LACAGPMGIG AIDYAINGGI QPSRVVVVDI DDKRLAQVQK LLPVELAASK GIELVYVNTK  240
GMSDPVQMLR ALTGDAGFDD IFVYAAVPAV VEMADELLAE DGCLNFFAGP TDKNFKVPFN  300
FYNVHYNSTH VVGTSGGSTD DMKEAIALSA TGQLQPSFMV THIGGLDAVP ETVLNLPDIP  360
GGKKLIYNGV TMPLTAIADF AEKGKTDPLF KELARLVEET HGIWNEQAEK YLLAQFGVDI  420
GEAAQ                                                              425

SEQ ID NO: 2            moltype = DNA  length = 1278
FEATURE                 Location/Qualifiers
source                  1..1278
                        mol_type = other DNA
                        organism = synthetic construct
SEQUENCE: 2
atgaaaacca aagttgctgc tatttatggc aagcgggatg tccgtctgcg cgtatttgaa  60
ctgccagaaa ttaccgataa tgaattactg gtgagtgtaa tttctgacag cgtctgttta  120
tcgacctgga aagcggcgtt actcggtagt gaacataaac gcgtacccga cgatttagaa  180
aatcatccgg tcattaccgg gcatgaatgt gccggggtta ttgtcgaagt gggtaaaaat  240
ctcactggca aatataaaaa aggccagcgt tttgtattgc aaccggcgat ggggttacca  300
agcagatatt cagcgggcta cagctacgaa tattttggcg gcaatgccac ttatatgatt  360
attcccgaaa tcgccattaa tttgggctgc gtattaccgt atcacggctc ttattttgct  420
gcggcgtcgc tggcagagcc tatgtgctgc attattggtg cttatcatgc caattatcac  480
accacgcaat atgtttatga gcatcgcatg ggcgtcaaac ctggcggcaa tattgcactg  540
ctggcgtgtg caggtccgat gggcattggc gctatcgatt acgccattaa cggcggcata  600
caaccgtcgc gggtggtggt ggtcgatatc gacgacaaac gtctggcgca ggtacagaag  660
ctgctgccgg tggaactggc ggccagtaaa ggcattgagc tggtgtatgt gaataccaaa  720
gggatgagcg atcctgtcca gatgctgcgg gcgctgacag gagatgccgg gttcgatgac  780
atttttgttt atgcggcggt gcctgctgtc gttgagatgg ctgatgaatt actggcggaa  840
gatggctgtc tgaacttctt tgccgggccg acggataaaa acttcaaagt gccgtttaat  900
ttctacaacg tccattacaa cagcacgcac gtcgtcggta catctggcgg ttcaacggac  960
gacatgaaag aggcgattgc ccttagcgcc actgggcagt tacagccgtc gtttatggtg  1020
acccatatcg gtggcctgga tgcggtgcca gaaaccgtgc tcaatctgcc ggatatccct  1080
ggcggtaaaa aactcattta taacggcgtg accatgccgc tcactgccat tgccgatttt  1140
gccgaaaaag gcaaaaccga tccgctgttt aaagagttgg cgcggctggt tgaggaaacg  1200
cacggcatct ggaatgaaca ggccgagaaa tatctgctgg cacaatttgg cgttgatatc  1260
ggggaggccg cgcaatga                                                1278

SEQ ID NO: 3            moltype = AA  length = 425
FEATURE                 Location/Qualifiers
source                  1..425
                        mol_type = protein
                        organism = Escherichia coli
SEQUENCE: 3
MKTKVAAIYG KRDVRLRVFE LPEITDNELL VSVISDSVCL STWKAALLGS EHKRVPDDLE  60
NHPVITGHEC AGVIVEVGKN LTGKYKKGQR FVLQPAMGLP SGYSAGYSYE YFGGNATYMI  120
IPEIAINLGC VLPYHGSYFA AASLAEPMCC IIGAYHANYH TTQYVYEHRM GVKPGGNIAL  180
LACAGPMGIG AIDYAINGGI QPSRVVVVDI DDKRLAQVQK LLPVELAASK GIELVYVNTK  240
GMSDPVQMLR ALTGDAGFDD IFVYAAVPAV VEMADELLAE DGCLNFFAGP TDKNFKVPFN  300
FYNVHYNSTH VVGTSGGSTD DMKEAIALSA TGQLQPSFMV THIGGLDAVP ETVLNLPDIP  360
GGKKLIYNGV TMPLTAIADF AEKGKTDPLF KELARLVEET HGIWNEQAEK YLLAQFGVDI  420
GEAAQ                                                              425

SEQ ID NO: 4            moltype = DNA  length = 1278
FEATURE                 Location/Qualifiers
source                  1..1278
                        mol_type = genomic DNA
                        organism = Escherichia coli
SEQUENCE: 4
atgaaaacca aagttgctgc tatttatggc aagcgggatg tccgtctgcg cgtatttgaa  60
ctgccagaaa ttaccgataa tgaattactg gtgagtgtaa tttctgacag cgtctgttta  120
tcgacctgga aagcggcgtt actcggtagt gaacataaac gcgtacccga cgatttagaa  180
aatcatccgg tcattaccgg gcatgaatgt gccggggtta ttgtcgaagt gggtaaaaat  240
ctcactggca aatataaaaa aggccagcgt tttgtattgc aaccggcgat ggggttacca  300
agcggatatt cagcgggcta cagctacgaa tattttggcg gcaatgccac ttatatgatt  360
attcccgaaa tcgccattaa tttgggctgc gtattaccgt atcacggctc ttattttgct  420
gcggcgtcgc tggcagagcc tatgtgctgc attattggtg cttatcatgc caattatcac  480
accacgcaat atgtttatga gcatcgcatg ggcgtcaaac ctggcggcaa tattgcactg  540
ctggcgtgtg caggtccgat gggcattggc gctatcgatt acgccattaa cggcggcata  600
caaccgtcgc gggtggtggt ggtcgatatc gacgacaaac gtctggcgca ggtacagaag  660
ctgctgccgg tggaactggc ggccagtaaa ggcattgagc tggtgtatgt gaataccaaa  720
gggatgagcg atcctgtcca gatgctgcgg gcgctgacag gagatgccgg gttcgatgac  780
atttttgttt atgcggcggt gcctgctgtc gttgagatgg ctgatgaatt actggcggaa  840
gatggctgtc tgaacttctt tgccgggccg acggataaaa acttcaaagt gccgtttaat  900
ttctacaacg tccattacaa cagcacgcac gtcgtcggta catctggcgg ttcaacggac  960
gacatgaaag aggcgattgc ccttagcgcc actgggcagt tacagccgtc gtttatggtg  1020
acccatatcg gtggcctgga tgcggtgcca gaaaccgtgc tcaatctgcc ggatatccct  1080
ggcggtaaaa aactcattta taacggcgtg accatgccgc tcactgccat tgccgatttt  1140
gccgaaaaag gcaaaaccga tccgctgttt aaagagttgg cgcggctggt tgaggaaacg  1200
```

-continued

```
cacggcatct ggaatgaaca ggccgagaaa tatctgctgg cacaatttgg cgttgatatc  1260
ggggaggccg cgcaatga                                                1278

SEQ ID NO: 5            moltype = DNA  length = 30
FEATURE                 Location/Qualifiers
source                  1..30
                        mol_type = other DNA
                        organism = synthetic construct
SEQUENCE: 5
caattttatt atagtaattg actattatac                                   30

SEQ ID NO: 6            moltype = DNA  length = 40
FEATURE                 Location/Qualifiers
source                  1..40
                        mol_type = other DNA
                        organism = synthetic construct
SEQUENCE: 6
gcttggtaac caattttatt atagtaattg actattatac                        40

SEQ ID NO: 7            moltype = DNA  length = 40
FEATURE                 Location/Qualifiers
source                  1..40
                        mol_type = other DNA
                        organism = synthetic construct
SEQUENCE: 7
gttaccaagc ggatattcag gttttagagc tagaaatagc                        40

SEQ ID NO: 8            moltype = DNA  length = 30
FEATURE                 Location/Qualifiers
source                  1..30
                        mol_type = other DNA
                        organism = synthetic construct
SEQUENCE: 8
ggatattcag gttttagagc tagaaatagc                                   30

SEQ ID NO: 9            moltype = DNA  length = 21
FEATURE                 Location/Qualifiers
source                  1..21
                        mol_type = other DNA
                        organism = synthetic construct
SEQUENCE: 9
gagcctgtcg gcctacctgc t                                            21

SEQ ID NO: 10           moltype = DNA  length = 20
FEATURE                 Location/Qualifiers
source                  1..20
                        mol_type = other DNA
                        organism = synthetic construct
SEQUENCE: 10
cggccggcat gagcctgtcg                                              20

SEQ ID NO: 11           moltype = DNA  length = 30
FEATURE                 Location/Qualifiers
source                  1..30
                        mol_type = other DNA
                        organism = synthetic construct
SEQUENCE: 11
atgccggccg gctgctattt atggcaagcg                                   30

SEQ ID NO: 12           moltype = DNA  length = 20
FEATURE                 Location/Qualifiers
source                  1..20
                        mol_type = other DNA
                        organism = synthetic construct
SEQUENCE: 12
gctgctattt atggcaagcg                                              20

SEQ ID NO: 13           moltype = DNA  length = 20
FEATURE                 Location/Qualifiers
source                  1..20
                        mol_type = other DNA
                        organism = synthetic construct
SEQUENCE: 13
cccatcgccg gttgcaatac                                              20

SEQ ID NO: 14           moltype = DNA  length = 20
FEATURE                 Location/Qualifiers
source                  1..20
                        mol_type = other DNA
```

```
                       organism = synthetic construct
SEQUENCE: 14
gcttggtaac cccatcgccg                                              20

SEQ ID NO: 15          moltype = DNA  length = 30
FEATURE                Location/Qualifiers
source                 1..30
                       mol_type = other DNA
                       organism = synthetic construct
SEQUENCE: 15
gttaccaagc agatattcag cgggctacag                                   30

SEQ ID NO: 16          moltype = DNA  length = 20
FEATURE                Location/Qualifiers
source                 1..20
                       mol_type = other DNA
                       organism = synthetic construct
SEQUENCE: 16
agatattcag cgggctacag                                              20

SEQ ID NO: 17          moltype = DNA  length = 20
FEATURE                Location/Qualifiers
source                 1..20
                       mol_type = other DNA
                       organism = synthetic construct
SEQUENCE: 17
tgctcataaa catattgcgt                                              20

SEQ ID NO: 18          moltype = DNA  length = 20
FEATURE                Location/Qualifiers
source                 1..20
                       mol_type = other DNA
                       organism = synthetic construct
SEQUENCE: 18
gcccatgcga tgctcataaa                                              20

SEQ ID NO: 19          moltype = DNA  length = 33
FEATURE                Location/Qualifiers
source                 1..33
                       mol_type = other DNA
                       organism = synthetic construct
SEQUENCE: 19
tcgcatgggc gagctcctga aaatctcgat aac                               33

SEQ ID NO: 20          moltype = DNA  length = 23
FEATURE                Location/Qualifiers
source                 1..23
                       mol_type = other DNA
                       organism = synthetic construct
SEQUENCE: 20
gagctcctga aaatctcgat aac                                          23

SEQ ID NO: 21          moltype = DNA  length = 20
FEATURE                Location/Qualifiers
source                 1..20
                       mol_type = other DNA
                       organism = synthetic construct
SEQUENCE: 21
acgtgtgacg gataaaccac                                              20

SEQ ID NO: 22          moltype = DNA  length = 20
FEATURE                Location/Qualifiers
source                 1..20
                       mol_type = other DNA
                       organism = synthetic construct
SEQUENCE: 22
ttcacataca ccagctcaat                                              20

SEQ ID NO: 23          moltype = DNA  length = 3234
FEATURE                Location/Qualifiers
source                 1..3234
                       mol_type = other DNA
                       organism = synthetic construct
SEQUENCE: 23
tttccatagg ctccgccccc ctgacgagca tcacaaaaat cgacgctcaa gtcagaggtg  60
gcgaaacccg acaggactat aaagatacca ggcgtttccc cctggaagct ccctcgtgcg  120
ctctcctgtt ccgaccctgc cgcttaccgg atacctgtcc gcctttctcc cttcgggaag  180
cgtggcgctt tctcatagct cacgctgtag gtatctcagt tcggtgtagg tcgttcgctc  240
caagctgggc tgtgtgcacg aaccccccgt tcagcccgac cgctgcgcct tatccggtaa  300
```

-continued

```
ctatcgtctt gagtccaacc cggtaagaca cgacttatcg ccactggcag cagccactgg  360
taacaggatt agcagagcga ggtatgtagg cggtgctaca gagttcttga agtggtggcc  420
taactacggc tacactagaa ggacagtatt tggtatctgc gctctgctga agccagttac  480
cttcggaaaa agagttggta gctcttgatc cggcaaacaa accaccgctg gtagcggtgg  540
tttttttgtt tgcaagcagc agattacgcg cagaaaaaaa ggatctcaag aagatccttt  600
gatcttttct acggggtctg acgctcagtg gaacgaaaac tcacgttaag ggattttggt  660
catgagatta tcaaaaagga tcttcaccta gatcctttta aattaaaaat gaagttttaa  720
atcaatctaa agtatatatg agtaaacttg gtctgacagt taaaagattg acagtataat  780
agtcaattac tataataaaa ttgatgcgca ggtgaaacac ctgctgcagt tttagagcta  840
gaaatagcaa gttaaaataa ggctagtccg ttatcaactt gaaaaagtgg caccgagtcg  900
gtgctttttt tcgttttccg ggacgccctc gcggacgtgc tcatagtcca cgacgcccgt  960
gattttgtag ccctggccga cggccagcag gtaggccgac aggctcatgc cggccggagc  1020
tcctgaaaat ctcgataact caaaaaatac gcccggtagt gatcttattt cattatggtg  1080
aaagttggaa cctcttagga tcctctagat ttaagaagga gatatacata aaactccttc  1140
tgagctagtt ctctagcatt ctattatttt gattcgacac cttaataata gcagaaggag  1200
tttttacctg tcaaagaacc atcaaaccct tgatacacaa ggctttgacc taattttgaa  1260
aaatgatgtt gtttctatat agtatcaaga taagaaagaa aaggattttt cgctacgctc  1320
aaatcctttc ccgtcacggg cttctcaggg cgttttatgg cgggtctgct atgtggtgct  1380
atctgacttt ttgctgttca gcagttcctg ccctctgatt ttccagtctg accacttcgg  1440
attatcccgt gacaggtcat tcagactggc taatgcaccc agtaaggcag cggtatcatc  1500
aacggggtct gacgctcagt ggaacgaaaa ctcacgttaa gggattttgg tcatgagatt  1560
atcaaaaagg atcttcacct agatcctttt aaattaaaaa tgaagtttta aatcaatcta  1620
aagtatatat gagtaaactt ggtctgacag ttaccaatgc ttaatcagtg aggcacctat  1680
ctcagcgatc tgtctatttc gttcatccat agttgcctga ctccccgtcg tgtagataac  1740
tacgatacgg gagggcttac catctggccc cagtgctgca atgataccgc gagacccacg  1800
ctcaccggct ccagatttat cagcaataaa ccagccagcc ggaagggccg agcgcagaag  1860
tggtcctgca actttatccg cctccatcca gtctattaat tgttgccggg aagctagagt  1920
aagtagttcg ccagttaata gtttgcgcaa cgttgttgcc attgctacag gcatcgtggt  1980
gtcacgctcg tcgtttggta tggcttcatt cagctccggt tcccaacgat caaggcgagt  2040
tacatgatcc cccatgttgt gcaaaaaagc ggttagctcc ttcggtcctc cgatcgttgt  2100
cagaagtaag ttggccgcag tgttatcact catggttatg gcagcactgc ataattctct  2160
tactgtcatg ccatccgtaa gatgcttttc tgtgactggt gagtactcaa ccaagtcatt  2220
ctgagaatag tgtatgcggc gaccgagttg ctcttgcccg gcgtcaatac gggataatac  2280
cgcgccacat agcagaactt taaaagtgct catcattgga aaacgttctt cggggcgaaa  2340
actctcaagg atcttaccgc tgttgagatc cagttcgatg taacccactc gtgcacccaa  2400
ctgatcttca gcatctttta ctttcaccag cgtttctggg tgagcaaaaa caggaaggca  2460
aaatgccgca aaaaagggaa taagggcgac acggaaatgt tgaatactca tactcttcct  2520
ttttcaatat tattgaagca tttatcaggg ttattgtctc atgagcggat acatatttga  2580
atgtatttag aaaaataaac aaataggggt tccgcgcaca tttccccgaa aagtgccacc  2640
aaaaaaacac aaaagaccac atttttaat gtggtcttta ttcttcaact aaagcaccca  2700
ttagttcaac aaacgaaaat tggataaagt gggatatttt taaaatatat atttatgtta  2760
cagtaagctg cctcgcgcgt ttcggtgatg acggtgaaaa cctctgacac atgcagctcc  2820
cggagacggt cacagcttgt ctgtaagcgg atgccgggag cagacaagcc cgtcagggcg  2880
cgtcagcggg tgttggcggg tgtcggggcg cagccatgac ccagtcacgt agcgatagcg  2940
gagtgtatac tggcttaact atgcggcatc agagcagatt gtactgagag tgcaccatat  3000
gcggtgtgaa ataccgcaca gatgcgtaag gagaaaatac cgcatcaggc gctcttccgc  3060
ttcctcgctc actgactcgc tgcgctcggt cgttcggctg cggcgagcgg tatcagctca  3120
ctcaaaggcg gtaatacggt tatccacaga atcaggggat aacgcaggaa agaacatgtg  3180
agcaaaaggc cagcaaaagg ccaggaaccg taaaaaggcc gcgttgctgg cgtt        3234
```

```
SEQ ID NO: 24          moltype = DNA  length = 9656
FEATURE                Location/Qualifiers
source                 1..9656
                       mol_type = other DNA
                       organism = synthetic construct
SEQUENCE: 24
aaagccatga caaaaacgcg taacaaaagt gtctataatc acggcagaaa agtccacatt  60
gattatttgc acggcgtcac actttgctat gccatagcat ttttatccat aagattagcg  120
gatcctacct gacgcttttt atcgcaactc tctactgttt ctccataccc gtttttttgg  180
gaattcgagc tctaaggagg ttataaaaaa tggatattaa tactgaaact gagatcaagc  240
aaaagcattc actaaccccc tttcctgttt tcctaatcag cccggcattt cgcgggcgat  300
attttcacag ctatttcagg agttcagcca tgaacgctta ttacattcag gatcgtcttg  360
aggctcagag ctgggcgcgt cactaccagc agctcgcccg tgaagagaaa gaggcagaac  420
tggcagacga catggaaaaa ggcctgcccc agcacctgtt tgaatcgcta tgcatcgatc  480
atttgcaacg ccacggggcc agcaaaaaat ccattacccg tgcgtttgat gacgatgttg  540
agtttcagga gcgcatggca gaacacatcc ggtacatggt tgaaaccatt gctcaccacc  600
aggttgatat tgattcagag gtataaaacg aatgagtact gcactcgcaa cgctggctgg  660
gaagctggct gaacgtgtcg gcatggattc tgtcgaccca caggaactga tcaccactct  720
tcgccagacg gcatttaaag gtgatgccag cgatgcgcag ttcatcgcat tactgatcgt  780
tgccaaccag tacggcctta atccgtggac gaaagaaatt tacgcctttc ctgataagca  840
gaatggcatc gttccggtgg tgggcgttga tggctggtcc cgcatcatca atgaaaacca  900
gcagtttgat ggcatggact ttgagcagga caatgaatcc tgtacatgcc ggatttaccg  960
caaggaccgt aatcatccga tctgcgttac cgaatggatg gatgaatgcc gccgcgaacc  1020
attcaaaact cgcgaaggca gagaaatcac ggggccgtgg cagtcgcatc ccaaacggat  1080
gttacgtcat aaagccatga ttcagtgtgc ccgtctggcc ttcggatttg ctggtatcta  1140
tgacaaggat gaagccgagc gcattgtcga aaatactgca tacactgcag aacgtcagcc  1200
ggaacgcgac atcactccgg ttaacgatga aaccatgcag gagattaaca ctctgctgat  1260
cgccctggat aaaacatggg atgacgactt attgccgctc tgttcccaga tatttcgccg  1320
cgacattcgt gcatcgtcag aactgacaca ggccgaagca gtaaaagctc ttggattcct  1380
```

-continued

```
gaaacagaaa gccgcagagc agaaggtggc agcatgacac cggacattat cctgcagcgt  1440
accgggatcg atgtgagagc tgtcgaacag ggggatgatg cgtggcacaa attacggctc  1500
ggcgtcatca ccgcttcaga agttcacaac gtgatagcaa aaccccgctc cggaaagaag  1560
tggcctgaca tgaaaatgtc ctacttccac accctgcttg ctgaggtttg caccggtgtg  1620
gctccggaag ttaacgctaa agcactggcc tggggaaaac agtacgagaa cgacgccaga  1680
accctgtttg aattcacttc cggcgtgaat gttactgaat ccccgatcat ctatcgcgac  1740
gaaagtatgc gtaccgcctg ctctcccgat ggtttatgca gtgacggcaa cggccttgaa  1800
ctgaaatgcc cgtttacctc ccgggatttc atgaagttcc ggctcggtgg tttcgaggcc  1860
ataaagtcag cttacatggc ccaggtgcag tacagcatgt gggtgacgcg aaaaaatgcc  1920
tggtactttg ccaactatga cccgcgtatg aagcgtgaag gcctgcatta tgtcgtgatt  1980
gagcgggatg aaaagtacat ggcgagtttt gacgagatcg tgccggagtt catcgaaaaa  2040
atggacgagg cactggctga aattggtttt gtatttgggg agcaatggcg atgagatcta  2100
aagaggagaa aggatctatg gataagaaat actcaatagg cttagatatc ggcacaaata  2160
gcgtcggatg ggcggtgatc actgatgaat ataaggttcc gtctaaaaag ttcaaggttc  2220
tgggaaatac agaccgccac agtatcaaaa aaaatcttat aggggctctt ttatttgaca  2280
gtggagagac agcggaagcg actcgtctca aacggacagc tcgtagaagg tatacacgtc  2340
ggaagaatcg tatttgttat ctacaggaga tttttttcaaa tgagatggcg aaagtagatg  2400
atagtttctt tcatcgactt gaagagtctt ttttggtgga agaagacaag aagcatgaac  2460
gtcatcctat ttttggaaat atagtagatg aagttgctta tcatgagaaa tatccaacta  2520
tctatcatct gcgaaaaaaa ttggtagatt ctactgataa agcggatttg cgcttaatct  2580
atttggcctt agcgcatatg attaagtttc gtggtcattt tttgattgag ggagatttaa  2640
atcctgataa tagtgatgtg gacaaactat ttatccagtt ggtacaaacc tacaatcaat  2700
tatttgaaga aaaccctatt aacgcaagtg gagtagatgc taaagcgatt ctttctgcac  2760
gattgagtaa atcaagacga ttagaaaatc tcattgctca gctccccggt gagaagaaaa  2820
atggcttatt tgggaatctc attgctttgt cattgggttt gacccctaat tttaaatcaa  2880
attttgattt ggcagaagat gctaaattac agctttcaaa agatacttac gatgatgatt  2940
tagataattt attggcgcaa attggagatc aatatgctga tttgtttttg gcagctaaga  3000
atttatcaga tgctatttta ctttcagata tcctaagagt aaatactgaa ataactaagg  3060
ctcccctatc agcttcaatg attaaacgct acgatgaaca tcatcaagac ttgactcttt  3120
taaaagcttt agttcgacaa caacttccag aaaagtataa agaaatcttt tttgatcaat  3180
caaaaaacgg atatgcaggt tatattgatg ggggagctag ccaagaagaa ttttataaat  3240
ttatcaaacc aattttagaa aaaatggatg gtactgagga attattggtg aaactaaatc  3300
gtgaagattt gctgcgcaag caacggacct ttgacaacgg ctctattccc catcaaattc  3360
acttgggtga gctgcatgct attttgagaa gacaagaaga cttttatcca tttttaaaag  3420
acaatcgtga gaagattgaa aaaatcttga cttttcgaat tccttattat gttggtccat  3480
tggcgcgtgg caatagtcgt tttgcatgga tgactcggaa gtctgaagaa acaattaccc  3540
catggaattt tgaagaagtt gtcgataaag gtgcttcagc tcaatcattt attgaacgca  3600
tgacaaactt tgataaaaat cttccaaatg aaaaagtact accaaaacat agtttgcttt  3660
atgagtattt tacggtttat aacgaattga caaaggtcaa atatgttact gaaggaatgc  3720
gaaaaccagc atttctttca ggtgaacaga agaaagccat tgttgattta ctcttcaaaa  3780
caaatcgaaa agtaaccgtt aagcaattaa aagaagatta tttcaaaaaa atagaatgtt  3840
ttgatagtgt tgaaatttca ggagttgaag atagatttaa tgcttcatta ggtacctacc  3900
atgatttgct aaaaattatt aaagataaag attttttgga taatgaagaa aatgaagata  3960
tcttagagga tattgttttta acattgacct tatttgaaga tagggagatg attgaggaaa  4020
gacttaaaac atatgctcac ctctttgatg ataaggtgat gaaacagctt aaacgtcgcc  4080
gttatactgg ttggggacgt ttgtctcgaa aattgattaa tggtattagg gataagcaat  4140
ctggcaaaac aatattagat tttttgaaat cagatggttt tgccaatcgc aattttatgc  4200
agctgatcca tgatgatagt ttgacattta aagaagacat tcaaaaagca caagtgtctg  4260
gacaaggcga tagtttacat gaacatattg caaatttagc tggtagccct gctattaaaa  4320
aaggtatttt acagactgta aaagttgttg atgaattggt caaagtaatg gggcggcata  4380
agccagaaaa tatcgttatt gaaatggcac gtgaaaatca gacaactcaa aagggccaga  4440
aaaattcgcg agagcgtatg aaacgaatcg aagaaggtat caaagaatta ggaagtcaga  4500
ttcttaaaga gcatcctgtt gaaaatactc aattgcaaaa tgaaaagctc tatctctatt  4560
atctccaaaa tggaagagac atgtatgtgg accaagaatt agatattaat cgtttaagtg  4620
attatgatgt cgatcacatt gttccacaaa gtttccttaa agacgattca atagacaata  4680
aggtcttaac gcgttctgat aaaaatcgtg gtaaatcgga taacgttcca agtgaagaag  4740
tagtcaaaaa gatgaaaaac tattggagac aacttctaaa cgccaagtta atcactcaac  4800
gtaagtttga taatttaacg aaagctgaac gtggaggttt gagtgaactt gataaagctg  4860
gttttatcaa acgccaattg gttgaaactc gccaaatcac taagcatgtg gcacaaattt  4920
tggatagtcg catgaatact aaatacgatg aaaatgataa acttattcga gaggttaaag  4980
tgattacctt aaaatctaaa ttagtttctg acttccgaaa agatttccaa ttctataaag  5040
tacgtgagat taacaattac catcatgccc atgatgcgta tctaaatgcc gtcgttggaa  5100
ctgctttgat taagaaatat ccaaaacttg aatcggagtt tgtctatggt gattataaag  5160
tttatgatgt tcgtaaaatg attgctaagt ctgagcaaga aataggcaaa gcaaccgcaa  5220
aatatttctt ttactctaat atcatgaact tcttcaaaac agaaattaca cttgcaaatg  5280
gagagattcg caaacgccct ctaatcgaaa ctaatgggga aactggagaa attgtctggg  5340
ataaagggcg agattttgcc acagtgcgca aagtattgtc catgccccaa gtcaatattg  5400
tcaagaaaac agaagtacag acaggcggat tctccaagga gtcaatttta ccaaaaagaa  5460
attcggacaa gcttattgct cgtaaaaaag actgggatcc aaaaaaatat ggtggttttg  5520
atagtccaac ggtagcttat tcagtcctag tggttgctaa ggtggaaaaa gggaaatcga  5580
agaagttaaa atccgttaaa gagttactag ggatcacaat tatggaaaga agttcctttg  5640
aaaaaaatcc gattgacttt ttagaagcta aaggatataa ggaagttaaa aaagacttaa  5700
tcattaaact acctaaatat agtctttttg agttagaaaa cggtcgtaaa cggatgctgg  5760
ctagtgccgg agaattacaa aaaggaaatg agctggctct gccaagcaaa tatgtgaatt  5820
ttttatattt agctagtcat tatgaaaagt tgaagggtag tccagaagat aacgaacaaa  5880
aacaattgtt tgtggagcag cataagcatt atttagatga gattattgag caaatcagtg  5940
aattttctaa gcgtgttatt ttagcagatg ccaatttaga taaagttctt agtgcatata  6000
acaaacatag agacaaacca atacgtgaac aagcagaaaa tattattcat ttatttacgt  6060
tgacgaatct tggagctccc gctgctttta aatattttga tacaacaatt gatcgtaaac  6120
```

-continued

```
gatatacgtc tacaaaagaa gttttagatg ccactcttat ccatcaatcc atcactggtc  6180
tttatgaaac acgcattgat ttgagtcagc taggaggtga ctaacgcatc ctcacgataa  6240
tatccgggta ggcgcaatca ctttcgtcta ctccgttaca aagcgaggct gggtatttcc  6300
cggcctttct gttatccgaa atccactgaa agcacagcgg ctggctgagg agataaataa  6360
taaacgaggg gctgtatgca caaagcatct tctgttgagt taagaacgag tatcgagatg  6420
gcacatagcc ttgctcaaat tggaatcagg tttgtgccaa taccagtaga aacagacgaa  6480
gaatccatgg gtatggacag ttttcccttt gatatgtaac ggtgaacagt tgttctactt  6540
ttgtttgtta gtcttgatgc ttcactgata gatacaagag ccaaatctag taatatttta  6600
tctgattaat aagatgatct tcttgagatc gttttggtct gcgcgtaatc tcttgctctg  6660
aaaacgaaaa aaccgccttg cagggcggtt tttcgaaggt tctctgagct accaactctt  6720
tgaaccgagg taactggctt ggaggagcgc agtcaccaaa acttgtcctt tcagtttagc  6780
cttaaccggc gcatgacttc aagactaact cctctaaatc aattaccagt ggctgctgcc  6840
agtggtgctt ttgcatgtct ttccgggttg gactcaagac gatagttacc ggataaggcg  6900
cagcggtcgg actgaacggg gggttcgtgc atacagtcca gcttggagcg aactgcctac  6960
ccggaactga gtgtcaggcg tggaatgaga caaacgcggc cataacagcg gaatgacacc  7020
ggtaaaccga aaggcaggaa caggagagcg cacgagggag ccgccagggg gaaacgcctg  7080
gtatctttat agtcctgtcg ggtttcgcca ccactgattt gagcgtcaga tttcgtgatg  7140
cttgtcaggg gggcggagcc tatggaaaaa cggctttgcc gcggcccgc tgaatattcc  7200
ttttgtctcc gaccatcagg cacctgagtc gctgtctttt tcgtgacatt cagttcgctg  7260
cgctcacggc tctggcagtg aatgggggta aatggcacta caggcgcctt ttatggattc  7320
atgcaaggaa actacccata atacaagaaa agatgtggtc tttattcttc aactaaagca  7380
cccattagtt caacaaacga aaattggata aagtgggata tttttaaaat atatatttat  7440
gttacctggc agagcctgta ctttttacag tcggttttct aatgtcacta acctgccccg  7500
ttagtcgcca tttgcatcga tttattatga caacttgacg gctacatcat tcactttttc  7560
ttcacaaccg gcacggaact cgctcgggct ggccccggtg catttttaa atacccgcga  7620
gaaatagagt tgatcgtcaa aaccaacatt gcgaccgacg gtggcgatag gcatccgggt  7680
ggtgctcaaa agcagcttcg cctggctgat acgttggtcc tcgcgccagc ttaagacgct  7740
aatccctaac tgctggcgga aaagatgtga cagacgcgac ggcgacaagc aaacatgctg  7800
tgcgacgctg gcgatatcaa aattgctgtc tgccaggtga tcgctgatgt actgacaagc  7860
ctcgcgtacc cgattatcca tcggtggatg gagcgactcg ttaatcgctt ccatgcgccg  7920
cagtaacaat tgctcaagca gatttatcgc cagcagctcc gaatagcgcc cttccccttg  7980
cccggcgtta atgatttgcc caaacaggtc gctgaaatgc ggctggtgcg cttcatccgg  8040
gcgaaagaac cccgtattgg caaatattga cggccagtta agccattcat gccagtaggc  8100
gcgcggacga aagtaaaccc actggtgata ccattcgcga gcctccggat gacgaccgta  8160
gtgatgaatc tctcctggcg ggaacagcaa aatatcaccc ggtcggcaaa caaattctcg  8220
tccctgattt ttcaccaccc cctgaccgcg aatggtgaga ttgagaatat aacctttcat  8280
tcccagcggt cggtcgataa aaaaatcgag ataaccgttg gcctcaatcg gcgttaaacc  8340
cgccaccaga tgggcattaa acgagtatcc cggcagcagg ggatcatttt gcgcttcagc  8400
catacttttc atactcccgc cattcagaga agaaaccaat tgtccatatt gcatcagaca  8460
ttgccgtcac tgcgtctttt actggctctt ctcgctaacc aaaccggtaa ccccgcttat  8520
taaaagcatt ctgtaacaaa gcgggaccag taatagaaag tgagggagcc acggttgatg  8580
agagctttgt tgtaggtgga ccagttggtg attttgaact tttgctttgc cacggaacgg  8640
tctgcgttgt cgggaagatg cgtgatctga tccttcaact cagcaaaagt tcgatttatt  8700
caacaaagcc acgttgtgtc tcaaaatctc tgatgttaca ttgcacaaga taaaaatata  8760
tcatcatgaa caataaaact gtctgcttac ataaacagta atacaagggg tgttatgagc  8820
catattcaac gggaaacgtc ttgctcgagg ccgcgattaa attccaacat ggatgctgat  8880
ttatatgggt ataaatgggc tcgcgataat gtcgggcaat caggtgcgac aatctatcga  8940
ttgtatggga agcccgatgc gccagagttg tttctgaaac atggcaaagg tagcgttgcc  9000
aatgatgtta cagatgagat ggtcagacta aactggctga cggaatttat gcctcttccg  9060
accatcaagc attttatccg tactcctgat gatgcatggt tactcaccac tgcgatcccc  9120
gggaaaacag cattccaggt attagaagaa tatcctgatt caggtgaaaa tattgttgat  9180
gcgctggcag tgttcctgcg ccggttgcat tcgattcctg tttgtaattg tccttttaac  9240
agcgatcgcg tatttcgtct cgctcaggcg caatcacgaa tgaataacgg tttggttgat  9300
gcgagtgatt ttgatgacga gcgtaatggc tggcctgttg aacaagtctg gaaagaaatg  9360
cataagcttt tgccattctc accggattca gtcgtcactc atggtgattt ctcacttgat  9420
aaccttattt ttgacgaggg gaaattaata ggttgtattg atgttggacg agtcggaatc  9480
gcagaccgat accaggatct tgccatccta tggaactgcc tcggtgagtt ttctccttca  9540
ttacagaaac ggctttttca aaaatatggt attgataatc ctgatatgaa taaattgcag  9600
tttcatttga tgctcgatga gtttttctaa tcagaattgg ttaattggtt gtaaca      9656
```